United States Patent [19]

Kosugi et al.

[11] 4,378,017
[45] Mar. 29, 1983

[54] COMPOSITE MATERIAL OF DE-N-ACETYLATED CHITIN AND FIBROUS COLLAGEN

[75] Inventors: Junichi Kosugi; Tadaaki Kato, both of Tokyo; Masayuki Funabashi, Iwaki, all of Japan

[73] Assignee: Kureha Kagaku Kogyo Kabushiki Kaisha, Tokyo, Japan

[21] Appl. No.: 242,419

[22] Filed: Mar. 11, 1981

[30] Foreign Application Priority Data

Mar. 21, 1980 [JP] Japan ................................. 55-36711
Mar. 21, 1980 [JP] Japan ................................. 55-36712

[51] Int. Cl.³ .................. A61F 13/18; A61L 17/00; C07G 7/00; C08L 5/08
[52] U.S. Cl. ............................................ 424/35; 3/1; 128/335.5; 128/DIG. 8; 128/DIG. 22; 260/123.7; 424/36; 424/37; 424/359; 424/360; 424/361; 426/138; 426/140; 426/278; 426/656
[58] Field of Search ............... 128/DIG. 8, 335.5290, 128/296; 3/1; 424/35, 36, 359, 361, 37, 360; 426/138, 140, 278, 641, 656, 657; 260/123.7; 435/177; 428/357, 392

[56] References Cited

U.S. PATENT DOCUMENTS 3,523,027 8/1970 Hall .................................. 260/123.7
3,833,744 9/1974 Bomstein .
4,260,228 4/1981 Miyata ............................. 260/123.7
4,264,155 4/1981 Miyata ............................. 260/123.7
4,280,954 7/1981 Yannas et al. .................... 260/123.7

FOREIGN PATENT DOCUMENTS 1515963 6/1978 United Kingdom .

OTHER PUBLICATIONS

Patent Abstracts of Japan, vol. 3, No. 54, (1979), p. 141 C45.
Chemical Abstracts, vol. 76, No. 17, (1972), p. 344, 98205n.

*Primary Examiner*—James C. Cannon
*Attorney, Agent, or Firm*—Wegner & Bretschneider

[57] ABSTRACT

A composite material of de-N-acetylated chitin and fibrous collagen, which may be prepared by bringing the de-N-acetylated chitin and the fibrous collagen into mutual contact in an aqueous acidic medium followed by deacidifying the obtained product, the fibrous collagen being able to be partially replaced by gelatin and/or soluble collagen, and a shaped material derived from the composite material is excellent in mechanical strength, heat-resistance and biostability and advantageously employed in the field of medical materials, edibles such as edible casing and base materials for inmobilizing enzyme.

14 Claims, No Drawings

COMPOSITE MATERIAL OF DE-N-ACETYLATED CHITIN AND FIBROUS COLLAGEN

This invention relates to a novel composite material comprising de-N-acetylated chitin and fibrous collagen which may be partially replaced by gelatin or soluble collagen. More particularly, the invention relates to a composite derived from the combination of the de-N-acetylated chitin, the fibrous collagen, the gelatin and the soluble collagen, which is excellent in mechanical strength and heat-resistance and is not absorbed by a living body.

A representative protein of collagen is a scleroprotein contained in the connective tissues, bones, teeth, ligaments, tendons, cutises, fasciae, etc. of mammals, birds, etc. and broadly employed in the forms of edible casing material, threads for surgical suture, pieces for vasculoplastic transplantation or artificial skins, etc. Collagen is superior to other materials used in such fields, however, it is not always satisfactory for those purposes.

For instance, as a casing material for foods such as ham and sausage which necessitate smoke-drying, gut of cattle, swine, sheep, etc., i.e., natural collagen material has been utilized. However, there is a limit in the production of a shaped material from the natural collagen material and since the shaped material is produced via various complicated and troublesome steps of treatment, it is highly expensive. Besides, since the shape and quality of natural material of collagen are irregular, respectively, such a material of natural collagen has scarcely been applied on a conventional high-speed meat-stuffing machine in the production of ham and sausage.

A tubely shaped material made of collagen fibers, i.e., an artificial collagen casing has been proposed to resolve the above-mentioned demerits. However, such an artificial collagen fiber is poor in film-forming property. Besides, such an artificial collagen casing is large in thickness because of the necessity of retaining its mechanical strength and accordingly, there are demerits of not so good appearance and of remarkably impairing the dietary feeling. Further, in hams and sausages enclosed with such an artificial collagen casing, unfavorable phenomena of breaking during its heating for cooking and of ablation of the casing from the stuffed meat take place.

Recently, a process for further subjecting the artificial collagen casing to a treatment of crosslinking has also been proposed for resolving the problem in cooking. However, such a crosslinked collagen casing is not satisfactory in the dietal feeling, either.

On the other hand, surgical materials such as the thread for surgical suture, artificial skin and hemostatic material, etc. from the collagen material are still unsatisfactory in the point of biostability (a property of not being absorbed by living body) other than the problem of strength. The process for providing a biostability to a collagen material has been studied from various points, and there is a process having a step of crosslinking collagen. However, the shaped material from the thus cross-linked collagen is remarkably poorer in elasticity than those of conventional shaped material of collagen. In addition, the following process is under trial with an intension of resolving the above-mentioned problems by forming the polyion complex between collagen and a high polymeric substance having carboxyl group(s) or sulfate group(s):

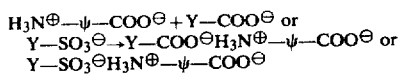

wherein $H_3N^{\oplus}$—ψ—$COO^{\ominus}$ represents ion of collagen molecule and Y—$COO^{\ominus}$ or Y—$SO_3^{\ominus}$ represents an ion of high polymeric substance.

The thus obtained polyion complex is excellent in biostability and has an antithrombogenic property. However, it dissolves into an aqueous medium, for example, an aqueous solution of an inorganic salt such as sodium chloride and is poor in mechanical properties. Accordingly, it is necessary to subject the polyion complex further to a treatment for stabilization such as crosslinking, etc.

The inventors of the present invention, during the course of studying the development of new composite materials suitable for use in broad range of purposes while reviewing the actual state of the art, have found out that a two-component composite comprising de-N-acetylated chitin and fibrous collagen or a multi-component composite comprising de-N-acetylated chitin, fibrous collagen and gelatin and/or soluble collagen, which may be prepared by bringing each proteinous substance into contact with the de-N-acetylated chitin, is extremely suitable to resolve the problems in the prior art.

Accordingly, the present invention provides a two-component composite comprising de-N-acetylated chitin and fibrous collagen wherein the amount of the de-N-acetylated chitin and the fibrous collagen is selected from the range of 0.01 to 99 and 1 to 99.99 parts by weight, respectively, to 100 parts by weight of the composite material, and provides a three- or four-component composite obtained by partially replacing the fibrous collagen of the two-component composite material with gelatin and/or soluble collagen wherein the amount of the gelatin and/or soluble collagen is up to 40 parts by weight to 100 parts by weight of the composite material and the amount of the de-N-acetylated chitin and the fibrous collagen is the same as in the two-component composite material. In addition, the present invention provides a method for preparing the above-mentioned composite material wherein the de-N-acetylated chitin and the proteinaceous substance of the fibrous collagen, the gelatin and the soluble collagen are brought into mutual contact in an aqueous acidic medium of pH 1 to 6, preferably pH 3 to 6 and then the obtained product is deacidified followed by cross-linking the deacidified product, if necessary.

Hitherto, proteinic composite materials such as those comprising collagen fiber and a soluble protein or comprising collagen fiber and gelatin, etc. have been reported. However, since in such a proteinic composition, the bonding between collagen and the soluble component is weak, the reduction of strength of such a composition is remarkable when the composition is brought into hot water. On the other hand, the composite material according to the present invention does not dissolve into an aqueous salt solution, and is excellent in mechanical strength which is not reduced particularly in hot water, in non-absorbability by living bodies, in blood-coagulating property, in resistance against the attack of bacteria, in film-forming ability and in close adhesion to stuffed materials such as meat.

Although it has not yet been elucidated why the composite material according to the present invention has an excellent mechanical properties, non-absorbability by living bodies and a blood-coagulating property, the existence of the strong bonding via the de-N-acetylated chitin and the proteinaceous substance of the fibrous collagen, the gelatin and the soluble collagen is presumed to form a stable polyion complex as follows:

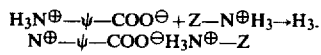

wherein $H_3N^\oplus$—$\psi$—$COO^\ominus$ represents an ion of the proteinaceous molecule and $H_3N^\oplus$—Z represents an ion of the de-N-acetylated chitin molecule.

The composite material according to the present invention is applicable to various usages. As one of such usages, an edible casing material is mentioned. Besides, as Kiriyama et al have reported in A.N.I. No. 71, since chitosan has the following physiological activities:

(a) returning the raised level of serum cholesterol to normal state,
(b) inhibiting the raising of the level of blood sugar,
(c) removing growth-inhibiting substances and
(d) preventing the colonal cancer, the composite material according to the present invention may be added to foods in the form of a spherically shaped material or a fibrous material, or may exhibit the preventive or therapeutic effects to the various symptoms such as (a) to (d) as an edible material.

Furthermore, since the composite material according to the present invention is not absorbable by living bodies owing to one of its components, de-N-acetylated chitin, and also has a blood-coagulating property, it can be surgically or therapeutically applied in the forms of film, fiber and those having a three dimensional structure. Although the crosslinked or not-crosslinked composite material of the present invention is itself thrombogenic, it can be applied as an anti-thrombogenic material after being heparin-treated and possibly applied as a medical material for artificial vessels, artificial skins, artificial kidneys, etc.

In addition, since the composite material according to the present invention is excellent in adsorbing proteins, it is possibly applicable as a base material for inmobilizing enzymes and microorganisms or as an adsorbent of enzymes and microorganisms.

The following are the more precise description of the present invention.

The de-N-acetylated chitin mentioned in the present invention is, from the viewpoint of solubility and processability, of a degree of de-N-acetylation of 50 to 100%, preferably 70 to 100% and of a viscosity of 20 to 1000 cp, the viscosity being determined at 20° C. on an aqueous 1% solution of acetic acid containing 0.5% by weight of the de-N-acetylated chitin. Commercialized chitosan may be used or the product obtained by treating chitin in an aqueous alkali solution of a high concentration while heating may be used, the chitin being obtained from shells of arthropods such as crabs, lobsters, shrimps, etc. by a conventional manner of separation and purification.

Protein mentioned in the present invention means two kinds of proteins, one of which is the fibrous collagen insoluble in an aqueous solvent and the other is the protein soluble in the aqueous solvent, i.e., gelatin and soluble collagen. They are hereinafter referred to as the proteinic component. The proteinic component is obtainable by separating and purifying proteinaceous tissues from living bodies of various animals, or by chemically treating the separated and purified protein. The aqueous solvent mentioned in the present invention is an aqueous solution of acid or alkali. As the acid, an inorganic acid such as hydrochloric acid, etc., a single organic acid such as acetic acid, propionic acid, adipic acid or a mixture of more than two kinds of the organic acid can be exemplified. The alkali means a conventional alkali such as sodium hydroxide, potassium hydroxide, etc.

Collagen fiber has been obtained by removing non-collageniccomponents from the fibrous components constituting major protein which is present in the connecting tissues of animals with chemical and mechanical treatments. Collagen fiber, for example, may be prepared by a process wherein bovine hide or bovine Achilles tendon, after having subjected to depilating treatment, is finely cut by a mincing machine and is swollen in an aqueous acidic or alkaline medium, and then is disintegrated by a grinder to obtain an aqueous dispersion, followed by filtration, if necessary.

In addition, it is preferable for the improvement of strength and homogenization of the produced composite material to subject the thus finely cut hide or tendon to a pretreatment.

As a process of the pretreatment, crosslinking of amino group of lysine residue in collagen by a crosslinking agent such as formaldehyde, glutaraldehyde, dialdehyde starch, glyoxal, smoke-drying liquid, epihalohydrin, etc., succinylation of the amino group by succinic anhydride, acylation of the amino group by carboxylic acid anhydride or esterification of carboxyl group in the side chain of aspartic acid residue or glutamic acid residue in collagen are mentioned.

Besides, as the raw material for collagen fiber, chips and rubbishes remaining after preparation of natural or artificial collagen casing, which are not utilizable for the casing are mentioned.

The fibrous collagen in the present invention is of 1 to 3$\mu$ in diameter and of 0.1 to 15 mm in length and of 5,000 to 1,000,000, preferably 20,000 to 500,000 in molecular weight, however, not necessarily being restricted within such ranges.

On the other hand, the other proteinic component of gelatin in the present invention may be one used in an industrial scale in food industries. The soluble collagen hereinmentioned is soluble in an aqueous solvent and may be obtained by treating the fibrous collagen with proteinase, an acid or an alkali to be wholly soluble into the aqueous solvent. Besides, a partly solubilized product obtainable in the treatment of the fibrous collagen is usable as a mixture of the fibrous collagen and the soluble collagen.

The soluble protein of the gelatin and the soluble collagen amounts to 0 to 40 parts by weight to 100 parts by weight of the composite material according to the invention. When the amount of the gelatin, the soluble collagen or the mixture thereof is more than 40 parts by weight, the moisture content of the obtained composite material is so much that the maintaining of the shape of the composite material is difficult and the tensile strength is poor. The gelatin is preferable as the soluble protein, and the amount of the gelatin is preferably 5 to 30 parts by weight to 100 parts by weight of the composite material.

The soluble protein, as a component of the composite material, contributes to the pliability, the reduced thermal deformation temperature, the improved mechanical strength, and also the improved dietary feeling of the composite material.

The composite material according to the present invention is also available by at first bringing the de-N-acetylated chitin and the proteinic component into contact in a medium having pH value in the range of 1 to 6, preferably of 3 to 6 and then deacidifying of the product thus obtained followed by subjecting to cross-linking, if necessary.

The deacidifying treatment mentioned herein means the adjusting of the pH of the reaction product of the de-N-acetylated chitin and the proteinic component higher than the isoelectric point of the reaction product. The deacidificating treatment is, for instance, an addition of an alkaline solution such as sodium hydroxide, potassium hydroxide or ammonium hydroxide to bring the pH higher than 7, an addition of an aqueous solution of alkaline salt, a removal of the acid present in the reaction mixture by evaporation or a treatment by electrodeposition.

The gelatin obtained by denaturing collagen has various isoelectric point, its jelly strength, its ash content, etc. according to the process of denaturation treatment. Accordingly, in the case where the proteinaceous composite material is prepared by an electrodeposition method from the gelatin obtained by an acid-treatment, it is necessary to adjust the pH of the electrodeposition-controlling liquid higher than 7 to make the shaped composite material on the cathode. On the other hand, in the case where the gelatin obtained by alkali-treatment is used, the shaped composite material must be formed on the anode by adjusting the pH of the electrodeposition-controlling liquid lower than 7.

Whereas, in the present invention, the composite material can also be prepared by electrodeposition without the above-mentioned restriction owing to the action of the de-N-acetylated chitin which is one of the components of the composition. Meanwhile, as the gelatin for use in the case of shaping by electrodeposition, a product containing less than 0.5% by weight of ash, preferably less than 0.2% by weight of ash is desirable from the viewpoints of quality and demand of electricity in preparation.

Besides, according to the process of the present invention, by combining the proteinic component which has been insufficient in shape-forming property with the de-N-acetylated chitin, the shape-forming property, for example, membrane-forming property can be improved and the problems concerning the preparation of the composite material such as the yield in the preparation, the stability and the uniformity of the product are possibly improved. Besides, since the remnant free aldehyde after the pretreatment of the fibrous collagen by the cross-linking is also reacted with the de-N-acetylated chitin according to the invention, the composite material is desirable from the viewpoint of safety.

The following are the more detailed explanation in preparing the composite material of the present invention.

As one of the embodiments of the contact of the proteinic component and the de-N-acetylated chitin, a process comprising the steps of mixing an acid medium containing the de-N-acetylated chitin and a medium containing a proteinic component and dispersing the mixture can be exemplified. In this case, the concentration of the de-N-acetylated chitin in the acidic medium is less than 5% by weight, preferably less than 1% by weight in connection to its viscosity (the medium being an aqueous dilute solution of acetic acid, hydrochloric acid, etc.), and the pH of the acidic medium is 1 to 6, preferably 3 to 6. It is not always necessary that the de-N-acetylated chitin is homogeneously dissolved in the medium, and the de-N-acetylated chitin may be dispersed uniformly as a fibrous state. The medium containing the proteinic component may be prepared by dispersing the proteinic component into an aqueous acidic solution of hydrochloric acid, etc. and by adjusting the pH thereof at 3 to 6, preferably 3 to 4. However, the acidity of the medium is not necessarily required, that is, the medium may be neutral or alkaline. In this case, it is finally necessary that the pH of the mixture of the medium containing the de-N-acetylated chitin and the medium containing the proteinic component is in the acidic region. In addition, in the case of electrodeposition, the medium containing the proteinic component is use in an acidic state.

In the present invention, a film-like composite material is available by pouring the de-bubbled mixture of the medium containing the de-N-acetylated chitin and the medium containing the proteinic component onto a glass plate and then de-acidifying the poured mixture by the use of a drier with hot air. The film-like composite material is characterized in that its strength does not depend on the tensile direction, that is, longitudinal or transversal in spite of having the fibrous protein.

The above-mentioned characteristic feature of the film-like composite material according to the present invention can be exhibited by the presence of the de-N-acetylated chitin in the composite material.

The spherically shaped composite material is prepared by dropping the de-bubbled mixture of the two media into a hydrophobic organic solvent such as toluene or xylene and then treating the thus formed material with an aqueous alcoholic solution to deacidify the spherically shaped material. Furthermore, fiber-like, film-like or hollowed composite material is possibly prepared by extruding the mixture from a hole-like or slit-like nozzle(s) into an aqueous solution of sodium chloride or ammonium hydroxide at a high concentration. In addition, the formed composite material of the present invention can be obtained by electrodeposition in which an aqueous medium containing the de-N-acetylated chitin and the proteinic component is introduced into an electrolytic cell provided with at least one cathode and at least one anode, and a direct voltage is loaded between both the electrodes to make the composite material accumulated on the surface of the predetermined electrode.

The tube-like composite material according to the present invention has an extremely thin wall membrane excellent in strength, and accordingly, it is highly suitable for edible casing material with a desirable dietary feeling.

In the case where the composite material according to the present invention is used for the edible casing, it is preferable that the amount of the de-N-acetylated chitin is selected from the range of 0.01 to 60 parts by weight, that of the fibrous collagen is selected from the range of 40 to 99.99 parts by weight and, if employed, that of the soluble protein of the gelatin, the soluble collagen or the mixture thereof is selected from the range of 5 to 30 parts by weight to 100 parts by weight of the composite material from the view points of the dietary feeling, the strength at smoke-drying and cooking, the thermal deformation temperature and the heat-stability of the casing. On the other hand, in the case where the composite material according to the present invention is used as a food additive, the amount of the de-N-acetylated chitin is selected from the range of 1 to 99 parts by weight to 100 parts by weight of the composite material and it is preferable to increase the amount of the de-N-acetylated chitin.

As another embodiment of the contact of the proteinic component and de-N-acetylated chitin, a process is exemplified in which a preliminarily shaped proteinic material into sheets, films, tubes, fiber-like forms, etc. is immersed into a acidified medium containing the de-N-acetylated chitin and then the shaped material is subjected to deacidifying treatment. In this case, since the superficial part of the composite material is composed of the de-N-acetylated chitin component, such as shaped composite material shows extremely unique properties such as improved mechanical properties, improved thermal resistance and antibacterial property.

Furthermore, in the case where the composite material according to the present invention obtained by one of the above-mentioned several methods is further subjected to a crosslinking treatment, the thus crosslinked composite material exhibits an improved property in blood-coagulation and an improved resistance to acids.

In the crosslinking treatment, a composite material according to the present invention is immersed into an aqueous solution prepared by dissolving a crosslinking agent into a buffer solution of phosphoric acid at a pH of 7.4 for 0.1 to 1 hour at 10° to 50° C. After the crosslinking is over, by washing the crosslinked material with water, a water-insoluble crosslinked composite material is obtained.

Since it is possible by such a process of crosslinking to cause not only the crosslinking of the de-N-acetylated chitin but also the crosslinking between the de-N-acetylated chitin and the proteinic component, an improved bonding force in the surface of the composite material is obtained. The crosslinking occurs between the same or the different functional groups among amino groups and hydroxyl groups in the de-N-acetylated chitin and collagen. As a crosslinking agent, the same agents mentioned in the crosslinking carried out in the pretreatment of the fibrous collagen are equally mentioned.

The present invention provides a novel composite material by combining the proteinic component and the de-N-acetylated chitin, which has excellent specific properties more than compensating the demerits of the de-N-acetylated chitin and the proteinic component, and the present invention contributes greatly to industries because the de-N-acetylated chitin is present in nature in abundance, however, owing to its high crystalinity and chemical stability, it has been utilized only in narrowly restricted fields.

EXAMLE 1

After immersing 100 kg of a salted steer hide into water for 15 hours, washing by water, and defatting, 90 kg of the thus treated hide was immersed into 450 kg of an aqueous liquid containing 2% by weight of calcium hydroxide, 0.5% by weight of sodium sulfide and 0.5% by weight of diethylamine at 25° C. for 24 hours while gently stirring the mixture. The thus treated hide was subjected successively to a depilating roll to remove hairs and decomposition products formed by the treatment with calcium hydroxide, to a splitting machine to roughly divide the hide, to a meat slicer to cut the divided hide into tapes of 5 mm in width and then to a mincing machine to cut the tapes into 5 cm in length.

Eighty kilograms of the thus obtained hide (referred to the refined hide hereinafter) were dispersed into 800 kg of water, and 3 kg of acetic acid were added to the dispersion and then after stirring gently for 12 hours, the refined hide was separated from the liquid, dehydrated by centrifugation and washed with de-ionized water until the electric conductivity of the washings became less than 20 $\mu\upsilon$/cm. At this time, the ash content of the refined hide was less than 0.1%. Forty kilograms of the thus treated refined hide were dispersed into 400 kg of an aqueous solution containing 0.015% by weight of glutaraldehyde and adjusted to pH of 3.0 by the addition of hydrochloric acid, and then crosslinked while stirring the solution gently for 12 hours at 20° C.

The crosslinked refined hide was collected by filtration with a wire netting and subjected to a pulp-refiner together wtih 113 kg of cold water to beat the fiber-bundles of the refined hide resulting in a dispersion of collagen fibers, to which hydrochloric acid was further added to make the pH thereof 3.0. The thus obtained dispersion weighing 125 kg contained 2.5% by weight of crosslinked collagen comprising a mixture of collagen fibers of 1 to 3$\mu$ in diameter and of 1 to 10 mm in length and still finer collagen fibriles.

Meanwhile, into 10 kg of an aqueous hydrochloric acid solution of pH of 3, one kg of de-N-acetylated chitin having a degree of de-N-acetylation of 95% were dissolved and after adjusting the pH of the solution to 3.0, 20 kg of an aqueous solution of de-N-acetylated chitin were obtained.

Into 1.5 kg of the aqueous dispersion of crosslinked collagen fiber, 50 kg of de-ionized water were added and the mixture was stirred at a high speed, and then, 374 g of the aqueous solution of de-N-acetylated chitin was added to the dispersion and the mixture was stirred for one hour to be an aqueous mixture containing collagen fiber and de-N-acetylated chitin at a weight ratio of 100/5, the viscosity and the electric conductivity of the aqueous mixture being 200 cP and 250 $\mu\upsilon$/cm, respectively.

From the aqueous mixture of collagen fiber and de-N-acetylated chitin, a tube-form membrane was formed by electrodeposition in which a membrane was formed on the cathode (17.5 mm$\phi$) by electrophoresis of collagen fiber and de-N-acetylated chitin. The thus formed membrane was pulled up, at the velocity of pulling up being 10 m/min.

The thus prepared tube-form membrane just after electrodeposition contained 2 g of water per g of the dry membrane and showed a tensile strength of 200 kg/cm$^2$.

The pulled-up membrane, after immersing into an aqueous 7% by weight of glycerol solution, was dried by a hot air at 75° C. for 2 min, while holding the tube-form membrane by pressured air of 300 mm H$_2$O, to be the composite material (Specimen A) according to the present invention.

On the othe hand, for comparison, a comparative tube-form membrane (Comparative Specimen A) consisting only of collagen fiber was prepared by the similar process mentioned above except for not adding de-N-acetylated chitin to crosslinked collagen fiber. The Comparative Specimen A contained 7 g of water per g of the dry membrane just after electrodeposition showing a tensile strength of 100 kg/cm$^2$.

The results of determination of tensile strength and tear strength in wet state of Specimen A and Comparative Specimen A according to the method described in JIS P-8113 and JIS P-8116 are shown in Table 1. As will be seen in Table 1, the specimen prepared from a mixture of crosslinked collagen fiber and de-N-acetylated chitin showed a remarkably improved tensile strength, and it was possible to obtain an extremely thin membrane.

Table 2 shows the results of strength-determination of the membranes by the same method as mentioned above after immersing into an aqueous 0.2N sodium chloride solution at 20° C. for 24 hours. As will be seen in Table 2, the composite material according to the present invention is superior to the Comparative Specimen A in strength, which suggests not only the ionic bonding between collagen fiber and de-N-acetylated chitin but also another bonding factor.

TABLE 1

| Specimen | Thickness of membrane ($\mu$) | Tensile strength (kg/cm$^2$) | Tear strength (g cm/cm) | Elongation at break (%) |
|---|---|---|---|---|
| Specimen A | 10 | 460 | 36 | 32 |
| Comparative Specimen A | 15 | 250 | 25 | 25 |

TABLE 2

| Specimen | Tensile strength (kg/cm$^2$) | Tear strength (g cm/cm) | Elongation at break (%) |
|---|---|---|---|
| Specimen A | 275 | 61 | 115 |
| Comparative Specimen A | 130 | 48 | 64 |

EXAMPLE 2

One kg of an acid-treated gelatin (lot number of F-795, manufactured by Miyagi Chem. Co. Ltd., Japan) was dissolved into 10 kg of an aqueous hydrochloric acid solution of pH of 3, and after adjusting the pH to 3.0, 20 kg of an aqueous solution of gelatin was obtained.

After adding 50 kg of de-ionized water to 15 kg of the aqueous dispersion of crosslinked collagen fiber prepared in Example 1 and stirring rapidly, 374 g of the aqueous solution of de-N-acetylated chitin prepared in Example 1 and 374 g of the aqueous solution of gelatin were further added to the dispersion of crosslinked collagen fiber, and the whole mixture was stirred for one hour to obtain an aqueous mixture of collagen fiber, de-N-acetylated chitin and gelatin at a weight ratio of collagen: de-N-acetylated chitin: gelatin of 100:5:5.

From the thus obtained aqueous mixture, a tube-form membrane was formed by the same method as in Example 1 (Specimen B).

For comparison, on the other hand, a comparative tube-form membrane (Comparative Specimen B) consisting of the collagen and gelatin was prepared by the same process, however, without adding de-N-acetylated chitin.

The results of determination of tensile strength and tear strength of the products by the same methods described in Example 1 in wet state are shown in Table 3. As is seen in Table 3, the strength of the membrane containing collagen fiber, de-N-acetylated chitin and gelatin was improved as compared to that of the membrane only containing collagen fiber and gelatin, thus showing the effect of added de-N-acetylated chitin.

Furthermore, the results of determination of the mechanical properties of the products after immersing them in warm water at 40° C. for 24 hours shown in Table 4 indicate the superiority of the composite material according to the present invention in strength to the product obtained without adding de-N-acetylated chitin.

TABLE 3

| Specimen | Thickness ($\mu$) | Tensile strength (kg/cm$^2$) | Tear strength (g cm/cm) | Elongation at break (%) |
|---|---|---|---|---|
| Specimen B | 10 | 480 | 36 | 35 |
| Comparative Specimen B | 10 | 340 | 27 | 27 |

TABLE 4

| Specimen | Tensile strength (kg/cm$^2$) | Tear strength (g cm/cm) | Elongation at break (%) |
|---|---|---|---|
| Specimen B | 370 | 60 | 110 |
| Comparative Specimen B | 140 | 45 | 60 |

EXAMPLE 3

A tube-form composite material (Specimen C) was prepared in the same manner as in Example 1 except for the weight ratio of the collagen fiber to de-N-acetylated chitin of 100/20 and a membrane-pulling-up velocity of 25 m/min. For comparison, a single material (a dispersion of collagen fiber of concentration of 0.58% by weight) was processed to be a membrane, however, the membrane could not be continuously pulled up.

The mechanical properties of Specimen C were: 8$\mu$ in thickness, 510 kg/cm$^2$ in tensile strength, 32% in elongation at break and 32 g cm/cm of tear strength.

EXAMPLE 4

A tube-form composite material (Specimen D) was prepared in the same manner as in Example 1 and 2 except for the weight ratio of collagen fiber: de-N-acetylated chitin: gelatin of 100:20:5 and a membrane-pulling-up velocity of 25 m/min. For comparison, an aqueous mixture of dispersed collagen fiber and gelatin of the weight ratio of collagen fiber: gelatin of 100:5 was tried to be a membrane, however, the membrane could not be continuousy pulled up. The mechanical properties of Specimen D were: 8$\mu$ in thickness, 490 kg/cm$^2$, in tensile strength, 33% in elongation at break and 33 g cm/cm in tear strength.

EXAMPLE 5

A tube-form composite material (Specimen E) was prepared in the same manner as in Example 1 and 2 except for using alkali-treated gelatin (lot number of F-800, Miyagi Chem. Co. Ltd., Japan) instead of acid-treated gelatin of Example 2 and the weight ratio of collagen fiber: gelatin: de-N-acetylated chitin of 100:20:10 and a membrane-pulling-up velocity of 15 m/min. For comparison, an aqueous mixture of collagen fiber and gelatin at a weight ratio of collagen to gelatin of 100:20 was subjected to electrodeposition, however, no membrane deposited on the electrode. The mechanical properties of Specimen E were: 9$\mu$ in thickness, 440 kg/cm$^2$ in tensile strength, 34% in elongation at break and 30 g cm/cm in tear strength.

EXAMPLE 6

After mixing 10 kg of the dispersion of crosslinked collagen fiber obtained in Example 1 and 1.5 kg of an aqueous 5% by weight of de-N-acetylated chitin solution obtained in Example 1 while stirring, the mixture was de-bubbled under a reduced pressure. The de-bubbled mixture was extruded from a slit of 10 cm in width and of 0.3 mm in height into an aqueous 0.1N ammonium hydroxide solution contained in a coagulation bath. The thus obtained film-form material was washed with water, and was treated in the same manner as in Example 1 to be a film-form composite material according to the present invention (Specimen F).

The results of the determination in a manner as in Example 1 were: $30\mu$ in thickness, 520 kg/cm² in tensile strength, 30% in elongation at break and 75 g cm/cm of tear strength.

On the other hand, a film prepared from the same dispersion of crosslinked collagen fiber in the same manner as above (Comparative Specimen C) without adding the solution of de-N-acetylated chitin showed the following properties: $30\mu$ in thickness, 200 kg/cm² in tensile strength, 26% in elongation at break and 48 g cm/cm in tear strength.

From the above-mentioned results, the composite material according to the present invention was confirmed to be superior to the single material (only consisting of crosslinked collagen fiber) in mechanical strength.

EXAMPLE 7

After mixing 10 kg of the dispersion of crosslinked collagen fiber obtained in Example 1, 1 kg of an aqueous 5% by weight gelatin solution obtained in Example 2 and 1.5 kg of an aqueous 5% by weight de-N-acetylated chitin solution obtained in Example 1, the mixture was well stirred and debubbled under a reduced pressure, and subjected to the same procedures as in Example 6 to obtain a film-form composite material according to the present invention (Specimen G). The mechanical properties of Specimen G in wet state were: $30\mu$ in thickness, 495 kg/cm² in tensile strength, 31% in elongation at break and 73 g cm/cm in tear strength. On the other hand, the membrane prepared from an aqueous mixture of collagen fiber and gelatin in the same manner as this example (Comparative Specimen D) showed mechanical properties of: $30\mu$ in thickness, 320 kg/cm² in tensile strength, 28% in elongation at break and 65 g cm/cm in tear strength.

The facts showed that the composite material according to the present invention is excellent in strength.

EXAMPLE 8

Aptitude test in mechanical stuffing

Practical tests were carried out on the tube-form Specimen C obtained in Example 3 and the tube-form Comparative Specimen A obtained in Example 1 by making them sausage-casing for a sausage meat of the following composition:

|  |  |
|---|---|
| salted pork meat | 1300 g |
| lard meat | 750 g |
| albumen | 90 g |
| iced water | 750 g |
| starch | 120 g |
| sodium glutamate | 9 g |
| allspice | 12 g |
| sucrose | 9 g |
| a phosphate | 6 g |
| pepper powder | 6 g |

Table 5 shows the results when the sausage meat was stuffed into the two kinds of sausage-casings (Specimen C and Comparative Specimen A) using a semi-automatic stuff-worker 760.

As is seen in Table 5, the casings prepared from a mixture of crosslinked collagen fiber and de-N-acetylated chitin (Specimen C) were able to withstand the severe conditions of stuffing. In addition, the knot on the sausage prepared from the sausage-casing according to the present invention (Specimen C) was smaller than that of from Comparative Specimen A and superior in appearance.

TABLE 5

| Sample* | Addition of de-N—acetylated chitin | Number of run** | Stuffed amount (g/piece) | Length of a sausage after stuffing (cm) | Rate of rupture |
|---|---|---|---|---|---|
| 1 | yes | 3 | 18 | 9.5 | 0 |
| 2 | yes | 9 | 20 | 9.8 | 0 |
| 3 | yes | 1 | 14.5 | 7.3 | 0 |
| 4 | yes | 1 | 17.5 | 8.4 | 0 |
| 5 | yes | 1 | 20 | 9.9 | 0 |
| 6 | yes | 1 | 23.5 | 11.8 | 0 |
| 7 | no | 1 | 17.2 | 9.5 | 0 |
| 8 | no | 2 | 19.4 | 10.5 | 1/400 |
| 9 | no | 1 | 15.4 | 7.4 | 1/250 |

Notes:
*Sample No. 1 to 6 used Specimen C according to the present invention. Sample No. 7 to 9 used Comparative Specimen A.
**By one run the tube-form material of 1000 m is produced in the electrodeposition procedure.

EXAMPLE 9

Aptitude test in mechanical stuffing

The same practical tests were carried out on the tube-formed Specimen D obtained in Example 4 and Comparative Specimen B obtained in Example 2 as sausage-casings with the same sausage meat as in Example 8. Table 6 shows the results of stuffing when the sausage meat was stuffed into the two kinds of sausage-casings (Specimen D and Comparative Specimen B) while using a semi-automatic stuff-worker 760.

As is seen in Table 6, the casings prepared from an aqueous mixture of dispersed collagen fiber and de-N-acetylated chitin and gelatin (Specimen D) according to the present invention were able to withstand the severe conditions of stuffing. In addition, the knot on the sausages prepared from the sausage-casing according to the present invention (Specimen D) was smaller than that of Comparative Specimen B and superior also in appearance.

TABLE 6

| Sample No. | Addition of de-N—acetylated chitin | Number of run | stuffed amount (g/piece) | Length of sausage (cm) | Rate of rupture |
|---|---|---|---|---|---|
| 1 | yes | 3 | 18 | 9.5 | 0 |
| 2 | yes | 9 | 20 | 9.8 | 0 |
| 3 | yes | 1 | 14.5 | 7.3 | 0 |
| 4 | yes | 1 | 17.5 | 8.4 | 0 |
| 5 | yes | 1 | 20 | 9.9 | 0 |
| 6 | yes | 1 | 23.5 | 11.8 | 0 |
| 7 | no | 1 | 17.2 | 9.5 | 0 |
| 8 | no | 2 | 19.4 | 10.5 | 1/1000 |

TABLE 6-continued

| Sample No. | Addition of de-N—acetylated chitin | Number of run | stuffed amount (g/piece) | Length of sausage (cm) | Rate of rupture |
|---|---|---|---|---|---|
| 9 | no | 1 | 15.4 | 7.4 | 1/500 |

EXAMPLE 10

Sausages of Sample No. 2 and No. 8 prepared in Example 8 were smoked as follows:

Pieces of sausage were hanged from a bar with eight rings in a chain-like state, and put into a smoking chamber. They were dried for 30 min at a controlled temperature of 55° to 60° C. at first, and then the temperature was raised to 75° C. while introducing a smoke generated from wood chips and further introducing steam into the chamber to control the humidity of the chamber at a constant level, the smoking treatment being continued for 30 min.

Then, steam was again introduced into the chamber to raise the temperature to 75° to 80° C. and after keeping the temperature for 50 min, the sausages were taken out from the chamber and cold water was sprayed onto the sausages to quench them.

The thus treated sausages were subjected to the following rupture tests under the simulated conditions of cooking of the sausages while supposing the cooking in homes by housewives:

(1) Fry-test

Into a frying pan provided with a temperature controller, an oil for frying was placed and while keeping the temperature of the oil at 160° C., every two sausages were put into the pan at a time in total 5 times (for preventing the reduction of the oil temperature), and the number of rupture of the ten sausages within 30 sec/time were counted.

(2) Frying pan test

A frying pan was set so that the bottom of the pan was immersed in an oil bath and was lower than the surface of the oil by 10 mm, and the temperature of the oil bath was controlled so that the surface of the pan was kept at 175° to 180° C.

Then, a small amount of the oil for frying was painted on the whole surface of the pan and every five sausages of the prepared ten sausages were put into the pan and moved within the pan slowly for 2 min, and the number of rupture of the sausage was counted. The test was carried out two times on the same specimen.

(3) Boiling test

While keeping water in a pot of 50 mm in depth at boiling, every five sausages of the prepared ten sausages were put into the pot and the number of rupture of the sausage within 5 min of boiling was counted. The test was carried out two times on the same Sample.

The results of the three kinds of tests are shown in Table 7.

TABLE 7

| Sample No. | Addition of de-N—acetylated chitin | Number of rupture per 10 sausages | | |
|---|---|---|---|---|
| | | Fry-test | Frying pan test | Boiling test |
| 2 | yes | 1 | 0 | 1 |
| 8 | no | 5 | 2 | 10 |

As is seen in Table 7, the sausage-casing of the material according to the present invention showed an excellent results also in practical cooking tests.

In order to support these practical facts, the respective membranes of these two kinds of sausage casing were immersed into a hot water at 75° C. for one min, and the percentage of their shrinkage and the thermal deformation temperature were determined. The results are shown in Table 8.

TABLE 8

| Specimen | Addition of de-N—acetylated chitin | Thermal deformation temperature (°C.) | Percent shrinkage | |
|---|---|---|---|---|
| | | | longitudinal direction | transversal direction |
| Specimen C | yes | 54.5 | 8.5 | 10.5 |
| Comparative Specimen A | no | 52 | 35.8 | 33.8 |

Besides, the sausage with the casing prepared from crosslinked collagen fiber added with de-N-acetylated chitin gives a feeling of mellow taste and sweetness when taken into one's mouth not hitherto have been felt on other sausages, for instance, with a membrane prepared from collagen fibers only.

EXAMPLE 11

In the same manner as in Example 1, tube-form materials having weight ratios of collagen fiber to de-N-acetylated chitin of 100/1 and 100/0.1, respectively, were prepared.

Into these tube-form materials, meat mixture was stuffed under the conditions of Sample No. 2 of Example 8 to be sausages, and the sausages were smoked in the same manner as in Example 10.

No rupture of the sausages was observed in stuffing, and the results of the cooking tests carried out as in Example 10 are shown in Table 9.

TABLE 9

| Amount of de-N—acetylated chitin added per 100 parts by weight of collagen fiber | Number of rupture per 10 sausage | | |
|---|---|---|---|
| | Test 1* | Test 2** | Test 3*** |
| 1 | 1 | 0 | 1 |
| 0.1 | 2 | 0 | 2 |

Notes:
Test 1*: Fry-test,
Test 2**: Frying pan test, and
Test 3***: Boiling test As is seen in Table 9, the composite material according to the present invention showed an excellent result even in practical cooking tests.

EXAMPLE 12

Sausages of Sample No. 2 and No. 8 prepared in Example 9 were smoked in the same manner as in Example 10. The smoked sausages were subjected to the rupture tests under the simulated conditions of cooking of the sausages while supposing the cooking in homes by housewives as in Example 10. The results of the three kinds of tests are shown in Table 10.

TABLE 10

| Sample No. | Addition of de-N—acetylated chitin | Number of rupture per 10 sausages | | |
|---|---|---|---|---|
| | | Fry-test | Frying pan-test | Boiling-test |
| 2 | yes | 1 | 0 | 3 |
| 8 | no | 3 | 2 | 10 |

As is seen in Table 10, the sausage-casing of the composite material according to the present invention showed an excellent results also in practical cooking tests.

Besides, when the thus prepared sausage from the aqueous mixture containing also de-N-acetylated chitin was taken into the consumer's mouth, a mellow taste and sweetness spreaded throughout the mouth giving an unparalleled feeling of eating never given by the sausages using only collagen as the casing material. In the sensory tests by a panel consisting of 30 persons, a general evaluation that no artificial feeling was given by the sausage stuffed in the casing of the composite material of the present invention as compared to the sausage stuffed into natural sheep gut was obtained.

EXAMPLE 13

Into 100 liters of acetic anhydride at a temperature of 15° C., 50 kg of the refined hide dehydrated by centrifuging in Example 1 were immersed for 8 hours to have collagen fiber acetylated. The thus treated refined hide was washed with flowing de-ionized water. The isoelectric point of the original steer hide of pH of 6.5 changed to 3.8 by the acetylation. An aqueous dispersion of collagen fibers was prepared from the acetylated hide in the same manner as in Example 1, the content of collagen being 2.5%.

An aqueous solution of de-N-acetylated chitin obtained in Example 1 was added to the thus prepared aqueous dispersion of collagen fiber in the same manner as in Example 1, however, with the ratio of collagen to de-N-acetylated chitin of 100/10 to prepare an aqueous mixture of collagen fiber and de-N-acetylated chitin.

An electrodeposited membrane was prepared from the aqueous mixture as in Example 1 with the same after-treatment as in Example 1.

The mechanical properties of the thus prepared tube-form membrane determined as in Example 1 were: $9\mu$ in thickness, 485 kg/c$^2$ in tensile strength, 33% in elongation at break and 35 g cm/cm in tear strength.

EXAMPLE 14

Using the refined hide dehydrated by centrifuging in the same manner as in Example 1, a 2.5% dispersion of collagen in water of pH of 3.0 was prepared as in Example 13, and then the aqueous solution of de-N-acetylated chitin obtained in Example 1 and the aqueous solution of gelatin obtained in Example 2 were added to the dispersion to obtain an aqueous mixture of dispersed collagen fiber and gelatin and de-N-acetylated chitin at a weight ratio of 100:10:10. The thus prepared aqueous mixture was subjected to electrodeposition in the same manner as in Example 1 to prepare a tube form membrane, one of the composite materials of the present invention.

The mechanical properties of the membrane determined as in Example 1 were: $9\mu$ in thickness, 480 kg/cm$^2$ in tensile strength, 33% in elongation at break and 34 g cm/cm in tear strength.

EXAMPLE 15

Into 20 liters of Atkins-Pantin buffer solution of pH of 9 containing 0.2% by weight of "Pronase" (manufactured by Kaken Chem. Co. Ltd., Japan), one kg of the refined hide obtained in Example 1 before crosslinking treatment was immersed for 24 hours under slow stirring to bring the hide into reaction with Pronase. After the reaction was over, the lumpy material was recovered by centrifugation and washed with water to purify. The purified material was dissolved into an aqueous 1N hydrochloric acid solution of pH of 3.5 to obtain 100 kg of an uniform solution of solubilized collagen. On the determination of the concentration of solubilized collagen in the solution by taking and examining a small portion of the solution after freeze-drying, it was known to be 0.95% by weight.

To 13.5 kg of the aqueous 2.5% crosslinked collagen dispersion prepared in Example 1, 50 kg of de-ionized water were added under high speed stirring, and 3.95 kg of the thus obtained aqueous solution of solubilized collagen were added to the mixture, and then the whole mixture was stirred for 30 min.

To the thus prepared mixture, 748 g of the aqueous de-N-acetylated chitin solution prepared in Example 1 and 374 g of the aqueous gelatin solution prepared in Example 2 were added, and the mixture was stirred well. In the thus prepared aqueous mixture, the weight ratio of collagen fibers: soluble collagen: gelatin: de-N-acetylated chitin was 90:10:10:20.

By subjecting the aqueous mixture to electrodeposition while using the apparatus used in Example 1, a composite material, i.e., a tube-form membrane, of the present invention was obtained of which the mechanical properties, determined as in Example 1, were: $9\mu$ in thickness, 500 kg/cm$^2$ in tensile strength, 35% in elongation at break and 35 g cm/cm in tear strength.

EXAMPLE 16

Into 50 g of an aqueous dispersion of 2.5% by weight of not-crosslinked collagen prepared following the procedures in Example 1, one gram of acidic protease was added, and after keeping the mixture for 5 hours at 37° C., the mixture was neutralized, subjected to centrifugation and the solid matter recovered was washed with water, and then adjusted to pH of 3.5 by the addition of an aqueous 1N hydrochloric acid solution. The thus prepared mixture weighing 1 kg was subjected to homogenization while keeping at lower than 10° C. to be further finely divided. The thus obtained liquid is hereinafter referred to as Liquid B.

A homogeneous solution of 20 g of de-N-acetylated chitin dissolved in an aqueous 5% by weight of acetic acid solution, hereinafter referred to as Liquid A, was added to Liquid B, and the mixture was processed to be a homogeneous solution by a homogenizer.

Into a 3-liter flask provided a stirrer, in which 2 liters of decahydronaphthalene and one gram of polyoxyethylene sorbitan (trade name ®Twin 80) were placed, 100 ml of the mixture of Liquid A and Liquid B was added, and the whole mixture was stirred at 1,000 rpm for one hour to be a dispersion. By re-dispersing the dispersion in 10 liters of ethanol, an insoluble matter was obtained. The insoluble matter was recovered by filtration and washed repeatedly with ethanol to remove the organic substances except ethanol, and the thus treated insoluble substance was re-dispersed into one liter of an aqueous 2% ammonium hydroxide solution. After neutralizing the dispersion, and recovering the precipitate by filtration and washing with water, spherical particles of a composite material according to the present invention were obtained (Specimen H) of particle size of 0.1 to 1.0 mm in diameter.

After freeze-drying Specimen H, one gram of dried Specimen H was put into an aqueous physiological saline solution, the solution was filtered off to recover the spherical particles.

The thus treated spherical particles were filled into a glass column of 8 mm in internal diameter, and then 50 ml of rabbit's blood added with 250 units of heparin were perfused through the column at a rate of 20 ml/min at 37° C. for 15 min. After stopping the circulation, the blood was removed from the column as soon as possible, and the column was washed with an aqueous physiological saline solution, and then the spherical particles were taken out from the column to examine the degree of adherence of platelets and blood corpuscles on the particles. The adherence of both the platelets and blood corpuscles were clearly recognized.

EXAMPLE 17

To 50 g of the aqueous dispersion of crosslinked collagen fiber prepared in Example 1, 7.5 g of the aqueous solution of gelatin of Example 2 were added, and after adjusting the pH of the mixture by the addition of an 1 N aqueous hydrochloric acid solution to 3.5, the mixture amounting to 1 kg was subjected at a temperature of lower than 10° C. to a homogenizer to be finely divided collagen therein, the thus prepared dispersion being referred to as liquid C.

A mixture of liquid C and liquid A of Example 16 was prepared and subjected to homogenization to obtain a homogeneous dispersion.

Into a 3-liter flask provided with a stirrer, in which 2 liters of decahydronaphthalene and one gram of polyoxyethylene sorbitan (Trade name ®Twin #80) were placed, 100 ml of the homogeneous dispersion of the mixture of Liquids C and A were introduced, and after one hour of stirring at 1000 rpm, the mixture was re-dispersed into 10 liters of ethanol to obtain an insoluble material. The insoluble material was collected by filtration and washed repeatedly with ethanol to remove decahydronaphthalene, and then, the washed material was again dispersed into one liter of an aqueous 2% ammonium hydroxide solution. On neutralizing the dispersion, spherical particles were deposited. The particles were collected by filtration, and washed with water to obtain a composite material of the present invention (Specimen K) as spherical particles of 0.1 to 1.0 mm in diameter.

Results of examination of the surface of the particles of Specimen K as in Example 16 showed the adherence of platelets and blood corpuscles on the surface of the particles, Specimen K.

EXAMPLE 18

After pouring the aqueous mixture of collagen fiber and de-N-acetylated chitin prepared in Example 6 onto a plate of 200 mm square to a thickness of 5 mm and leaving still for one hour, the plate with the mixture was immersed into an aqueous 0.1 N ammonium hydroxide solution to neutralize the acidity, and washed with de-ionized water to remove salts. The thus obtained material was immersed into an aqueous 0.1 M disodium phosphate solution containing 0.5% by weight of formaldehyde at 30° C. for one hour and then washed with water.

The thus obtained formed material was freeze-dried to be a sponge-form material. The sponge-form material showed an absorption of aqueous physiological saline solution of 20 g per g of the material and further, it shows a strong coagulation activity to bloods, and accordingly, it has been found that the material is possibly applicable as a menstrual pad material and as a garrot tourniquet for urgent cases.

EXAMPLE 19

The aqueous mixture of collagen fiber, gelatin and de-N-acetylated chitin of Example 2 was treated in the same manner as in Example 18 to obtain a spongy-form material. The thus obtained material showed an absorption ability to an aqueous physiological saline solution of 21 g/g material, and a strong coagulating property to human blood. Accordingly, it was found that the material is applicable as the material for menstrual pads and tourniquets for urgent cases.

EXAMPLE 20

Into a solution prepared by dissolving 1 g of glucoseisomerase(2000 U/g; manufactured by Nagase Sangyo Co. Ltd.) into an aqueous 0.1 M disodium phosphate solution, 30 g of the spherical particles (Specimen H of Example 16) were added, and after stirring the mixture for 2 hours at 5° C., 2 ml of an aqueous 25% by weight glutaraldehyde solution was added to the mixture. After leaving the mixture as it is for 5 hours, solid materials were recovered by filtration, washed with an aqueous phosphoric buffer solution of pH of 7.0 and added to 500 ml of an aqueous phosphoric buffer solution containing 2 g of glucose. After thus treating the mixture for 60 min at 70° C., the contents of glucose and fructose of the solid material were 600 and 1400 mg, respectively, together with the fixed enzyme (glucose-isomerase) of 70% of the applied amount.

In addition, separately, the pH of the solution of collagen and de-N-acetylated chitin before re-dispersion in Example 16 was adjusted to 6.0, and 1 g of glucose-isomerase was added to the solution at 5° C. After re-dispersing the mixture as in Example 16, the solid matter was recovered by filtration and washed with ethanol and then with an aqueous phosphoric buffer solution of pH of 7.0.

It was found that 85% of the enzyme (glucose-isomerase) applied was fixed onto the solid matter.

These results show that the thus obtained material is possibly applied as a carrier for fixed enzymes and microbial bodies.

EXAMPLE 21

The same procedures as in Example 20 were carried out except for using Specimen K obtained in Example 17 instead of Specimen H used in Example 20. The amounts of glucose and fructose on Specimen K after the treatment at 70° C. for 60 min were 600 and 1400 mg, respectively with the fixed rate of glucose isomerase of 70%.

From these results, it has been found that a composite material according to the present invention, i.e., Specimen K, is possibly applicable as a carrier of fixed enzymes and microbial bodies.

EXAMPLE 22

After immersing Comparative Specimen A comprising a shaped material consisting only of collagen fibers into a homogeneous solution of a viscosity of 50 cP prepared by adding 5 g of de-N-acetylated chitin having a degree of de-N-acetylation of 85% into one liter of an aqueous 1% acetic acid solution at 20° C. for one hour, the excess aqueous solution was removed, and the thus treated material in a wet state was once immersed into an aqueous 0.1 N ammonia solution. Then the shaped material was washed with water to remove the attached ammonium acetate and ammonia to obtain a composite material according to the present invention.

The composite material showed the following mechanical properties of 395 kg/cm$^2$ of tensile strength, 33% of elongation at break and 50 g cm/cm of tear strength. The immersed amount of de-N-acetylated chitin into collagen fibers was 2/100 by weight.

EXAMPLE 23

In the same manner as in Example 22 except for using Comparative Specimen B obtained in Example 2 and a solution (viscosity; 100 cP) of de-N-acetylated chitin having a degree of de-N-acetylation of 75%, a composite material of the present invention was obtained. The mechanical properties thereof were: 400 kg/cm$^2$ in tensile strength, 30% in elongation at break and 30 g cm/cm in tear strength. The content of de-N-acetylated chitin of the composite material obtained in this example was 2 parts per 100 parts of collagen fiber.

What is claimed is:

1. Composite thrombogenic, physiological saline solution-insoluble material of de-N-acetylated chitin and fibrous collagen.

2. Composite material of claim 1, wherein the fibrous collagen is partially replaced by gelatin and/or soluble collagen.

3. Composite material of claim 1 or 2, wherein the fibrous collagen is previously cross-linked or acylated.

4. Composite material of any one of claims 1 to 3, which is further cross-linked.

5. Edible material comprising the composite material of any one of claims 1 to 4.

6. Medical material comprising the composite material of any one of claims 1 to 4.

7. Base material for immobilizing enzyme, comprising the composite material of any one of claims 1 to 4.

8. A method for preparing a composite material of claim 1, comprising bringing de-N-acetylated chitin into contact with fibrous collagen in an acidic medium followed by deacidifying the obtained product.

9. A method of claim 8, wherein the contact of the de-N-acetylated chitin with the fibrous collagen is effected by mixing an aqueous acidic solution of the de-N-acetylated chitin and an aqueous dispersion of fibrous collagen.

10. A method of claim 8, wherein the contact of the de-N-acetylated chitin with the fibrous collagen is effected by immersing a previously shaped material of the fibrous collagen into an aqueous acidic solution of the de-N-acetylated chitin.

11. A method of any one of claims 8 to 10, wherein the fibrous collagen is partially replaced by gelatin and/or soluble collagen.

12. A method of claim 8, wherein the fibrous collagen is previously cross-linked or acylated before the contact with the de-N-acetylated chitin.

13. A method of claim 8, wherein the deacidifying is effected by the addition of an aqueous alkaline solution to said obtained product, by the removal of the acid in said acidic medium by evaporation, or by the electrodeposition of said obtained product wherein said acid is neutralized by OH$^-$ ions formed by said electrodeposition.

14. A method of claim 8, wherein the resultant composite material is further cross-linked.

* * * * *